US00PP36962P2

(12) United States Plant Patent
Smith

(10) Patent No.: US PP36,962 P2
(45) Date of Patent: Sep. 16, 2025

(54) ***PAEONIA* PLANT NAMED 'Smithopus8'**

(50) Latin Name: ***Paeonia* hybrid**
Varietal Denomination: Smithopus8

(71) Applicant: Donald R. Smith, Fairfield, CT (US)

(72) Inventor: Donald R. Smith, Fairfield, CT (US)

( * ) Notice: Subject to any disclaimer, the term of this patent is extended or adjusted under 35 U.S.C. 154(b) by 0 days.

(21) Appl. No.: 18/978,302

(22) Filed: Dec. 12, 2024

(51) Int. Cl.
*A01H 6/00* (2018.01)
*A01H 5/02* (2018.01)

(52) U.S. Cl.
USPC ..... Plt./316

(58) Field of Classification Search
USPC ..... Plt./316
CPC ..... A01H 6/00; A01H 5/02
See application file for complete search history.

*Primary Examiner* — Keith O. Robinson

(57) ABSTRACT

A new and distinct cultivar of intersectional hybrid (Itoh) *Paeonia* plant named 'Smithopus3' is disclosed, large pale yellow flowers flushed pink with a distinctive red basal flare of semi-double to fully double form carried on strong stems, which present the flowers above and beyond the foliage. Plants have very attractive, dissected foliage, which lasts through the fall and is also highly disease resistant. Plants have a symmetrical, compact plant habit/shape which is excellent in the landscape. The new variety is a intersectional hybrid (Itoh) *Paeonia* normally produced as an outdoor ornamental garden plant.

2 Drawing Sheets

Figure 1:
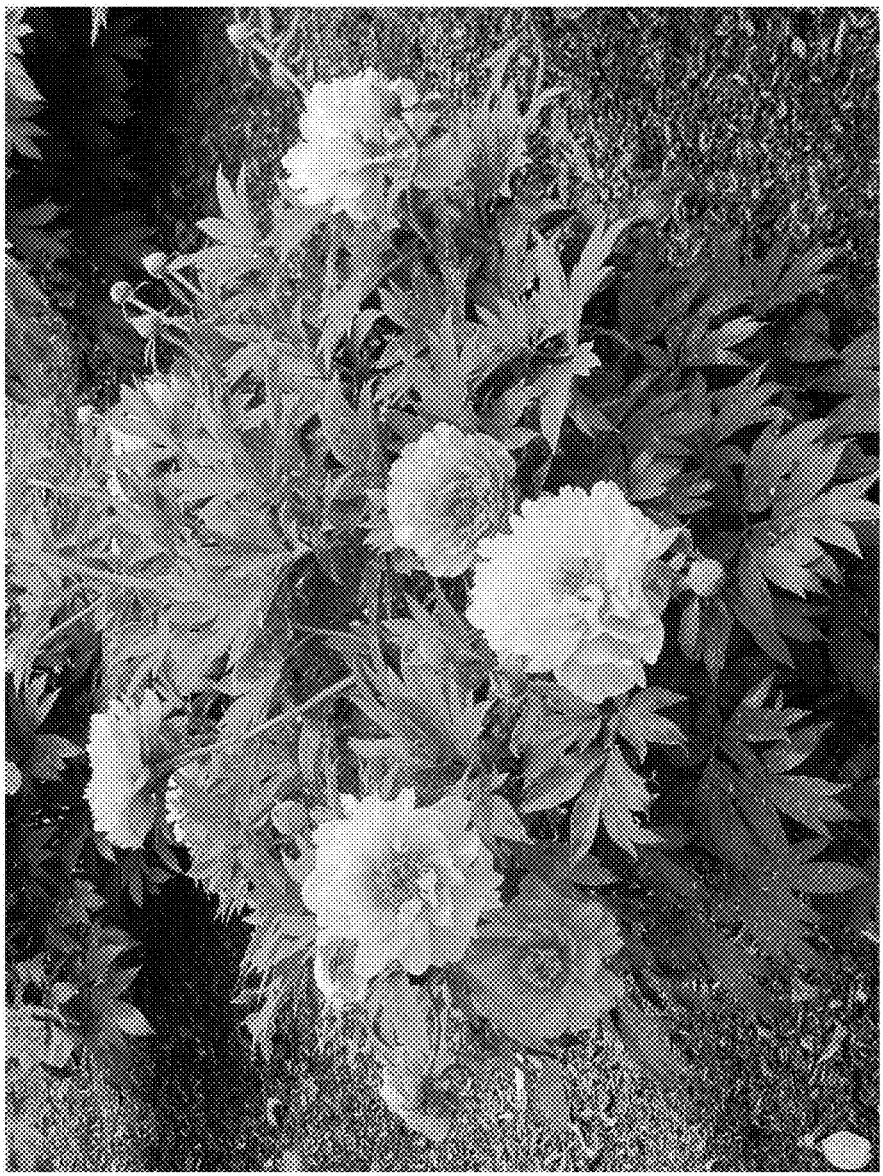

Latin name of the genus and species: *Paeonia* hybrid.
Variety denomination: 'Smithopus8'.

BACKGROUND OF THE INVENTION

The new cultivar is a product of a planned breeding program conducted by the inventor to produce new *Paeonia* hybrid cultivars with strong stems, large panicles, compact habits, and attractive flower aging. The crossing resulting in the new cultivar was made in summer of 1998 in a backyard in Windham, NH.

The seed parent is the cultivar *Paeonia* 'Martha W', unpatented. The pollen parent is the cultivar *Paeonia* 'Smith's Yellow', an unpatented tree peony hybrid. The new cultivar was found and selected by the inventor in 2012 in the same backyard in Windham, NH. Asexual reproduction of the new cultivar 'Smithopus8' was first performed at a research laboratory during 2014 in South Africa by tissue culture. Through subsequent confidential propagation, multiple additional generations have been reproduced, having shown that the unique features of this cultivar are stable and reproduced true to type.

Plants of the new cultivar were first sold Jul. 1, 2024 in the United States. This was from plant material originating from the inventor. Plants were advertised on a website from the Entity "Plants Nouveau", which has received a license, information and plant material directly from the inventor.

SUMMARY OF THE INVENTION

The cultivar 'Smithopus8' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Smithopus8'. These characteristics in combination distinguish 'Smithopus8' as a new and distinct *Paeonia* cultivar:

1. New cultivar is an intersectional hybrid (Itoh) peony from a cross of an herbaceous peony (lactiflora) with a hybrid tree peony.
2. It is a sterile first-generation hybrid with triploid (3n) ploidy level.
3. New cultivar has large pale yellow flowers that are heavily flushed with pink and are of semi-double to double form carried on strong stems, which present the flowers above and beyond the foliage.
4. New cultivar has very attractive, dissected foliage, which lasts through the fall and is also highly disease resistant.
5. New cultivar has a symmetrical, compact plant habit/shape and makes an ideal landscape plant.

PARENT COMPARISONS

Plants of 'Smithopus8' are similar to plants of the seed parent in most horticultural characteristics, however, plants of 'Smithopus8' differ in the following:

1. Seed parent has fully herbaceous stems and growth habit, whereas the new cultivar has stronger semi-woody to woody stems and many above-ground buds, yet grows primarily as an herbaceous plant.
2. Seed parent has pink flowers of single form with 11-13 petals, whereas the new cultivar has semi-double to double pale yellow flowers that are heavily flushed with pink with many more petals (about 30 to 40).
3. Seed parent blooms 1-2 weeks later than the new cultivar
4. Seed parent has many lateral flowers per stem, whereas the new cultivar has only 1 or 2.
5. Seed parent is highly fertile both ways, whereas the new cultivar is a sterile triploid Plants of 'Smithopus8' are similar to plants of the pollen parent in most horticultural characteristics, however, plants of 'Smithopus8' differ in the following:

1. The new cultivar has pale yellow flowers that are heavily flushed with pink; whereas 'Smith's Yellow' has bright yellow flowers that are lightly flushed with pink
2. Pollen parent is a woody tree peony hybrid that has winter hardy, woody stems, whereas the new cultivar has semi-woody stems that are much less winter hardy
3. Pollen parent has more upright, shrub-like plant and growth habit, whereas the new cultivar has mostly herbaceous habit
4. Pollen parent blooms 1-2 weeks before the new cultivar.

COMMERCIAL COMPARISON

Plants of 'Smithopus8' can be compared to plants of the commercial cultivar *Paeonia* intersectional hybrid 'Magical Mystery Tour', unpatented. Plants of 'Smithopus8' are similar to plants of 'Magical Mystery Tour' in most horticultural characteristics, however, plants of 'Smithopus8' differ in the following:

1. 'Magical Mystery Tour' and the new cultivar both have similar flower color combinations. However, in the intermediate stage, the new cultivar has more pale yellow coloration, whereas 'Magical Mystery Tour' is primarily pink.
2. The new cultivar also is more floriferous than 'Magical Mystery Tour', as a result of having more flowers from lateral stems.
3. The new cultivar has flowers that are more double than 'Magical Mystery Tour'.

Plants of 'Smithopus8' can be compared to plants of the commercial cultivar *Paeonia* intersectional hybrid 'Singing in the Rain II', U.S. Plant Pat. No. 19,374. Plants of 'Smithopus8' are similar to plants of 'Singing in the Rain II' in most horticultural characteristics, however, plants of 'Smithopus8' differ in the following:

1. 'Singing in the Rain II' has darker yellow flower petals without red basal flares, whereas the new cultivar has pale yellow flowers flushed pink with red basal flares.
2. 'Singing in the Rain II' has smaller flowers than the new cultivar.
3. 'Singing in the Rain II' has more flowers per stem than the new cultivar.

BRIEF DESCRIPTION OF THE PHOTOGRAPHS

The accompanying photograph in FIG. 1 illustrates in full color a typical plant of 'Smithopus8' grown in a field in Fairfield, CT. Flowers on this plant are slightly aging. This plant is approximately 3 years old.

Figure 2:
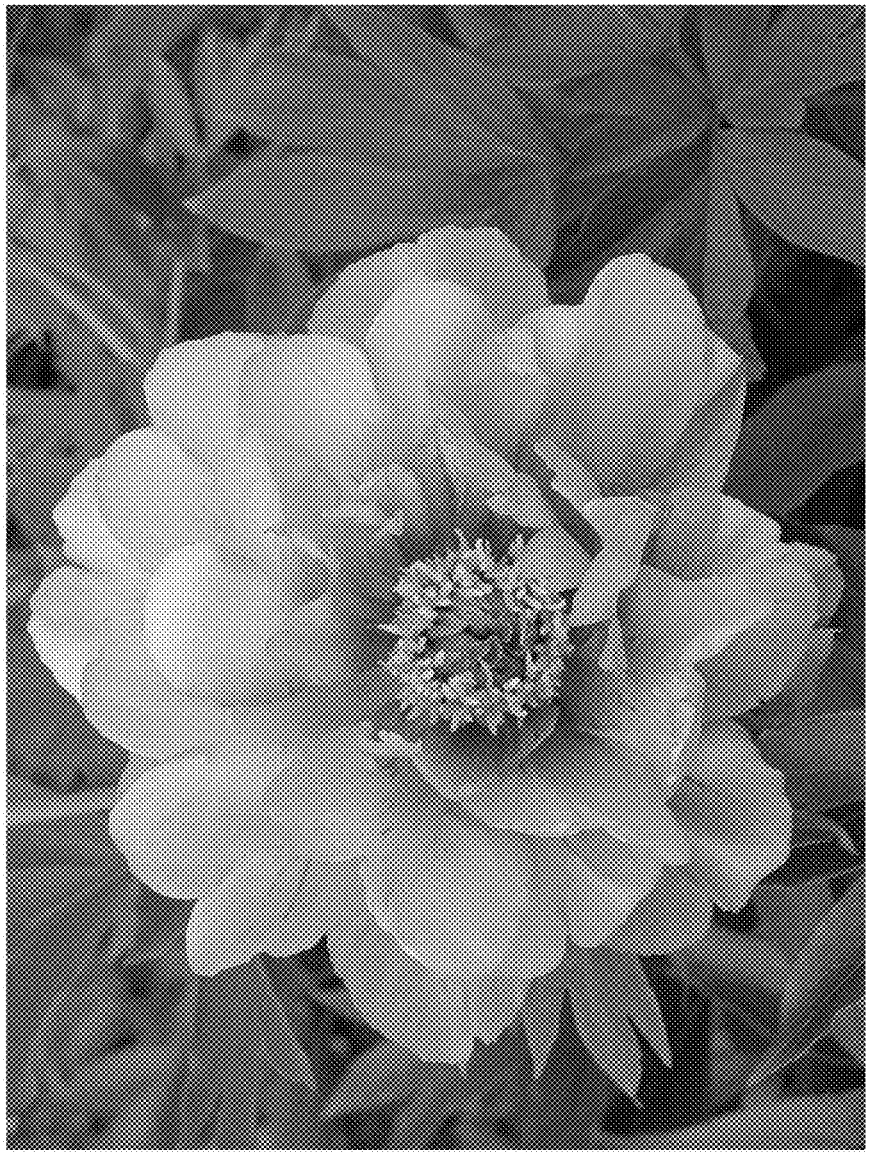

FIG. 2 illustrates in full color a close-up of a mature flower of 'Smithopus8'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'Smithopus8' plants grown outdoors in Camarillo, CA. The plants were 2 to 3 years old from large tubers, grown in 5-gallon pots. Temperatures ranged from 5° C. to 10° C. at night to 12° C. to 30° C. during the day. No artificial light, photoperiodic treatments were given to the plants. Measurements and numerical values represent averages of typical plant types.

Botanical classification: *Paeonia* hybrid 'Smithopus8'.

PROPAGATION

Typically by shoot tissue culture.

Root description: Freely branching storage root with numerous feeder roots. Roots various shades of tan and brown, not accurately measured with a color chart.

Tubers: Elongated, typically 4 to 10 cm long and 2 to 4 cm in diameter. Colored near Greyed-Orange 166C.

PLANT

Growth habit: Vigorous perennial herbaceous shrub. Semi-upright growth habit.

Height: Approximately 45 to 50 cm at opening of first flower.

Plant spread: Approximately 55 cm.

Stems:

Length: Approximately 22 to 35 cm.

Diameter: Average range 6 to 7 mm.

Strength: Strong.

Internode length: 5 to 11 cm, highly variable.

Color: Near RHS Green 138C lightly flushed Greyed-Red 181B.

Texture: Glabrous.

Age of plant described: Approximately 2 to 3 years.

FOLIAGE

Leaf: Alternate, pinnate compound, with an overall circular to ovate shape, which is slightly wider than long. Average fully expanded leaf 15 cm long and 18 cm wide, excluding the petiole. Horizontal to semi-erect attitude.

Primary leaflets:

*Shape*.—Obovate.

*Quantity and arrangement*.—3 primary leaflets further divided into 3 to 5 deeply divided secondary leaflets. All leaflets sessile.

*Length*.—Average range 8 to 10 cm.

*Width*.—Average range 7 to 10 cm.

Individual primary leaflet blades:

*Shape of blade*.—Broad ovate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very slightly reflexed downward.

Individual secondary leaflet blades:

*Shape of blade*.—Oblanceolate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.
*Appearance of bottom surface*.—Matte.
*Aspect*.—Flat to very minutely reflexed downward.
*Color*.—Young — Upper side: Near RHS Green 137D. Under side: Near RHS Green 138B. Mature — Upper side: Near RHS Green 137C. Under side: Near RHS Green 138A.
*Venation*.—Type: Pinnate. Venation color upper side: Near RHS Yellow-Green 144C. Venation color under side: Near RHS Yellow-Green 144C.
*Petiole*.—Length: Average range 5 to 8 cm. Diameter: 5 to 6 mm. Color: Near RHS Yellow-Green 144C lightly flushed Greyed-Red 181B. Texture: Glabrous.

FLOWER

Natural flowering season: Flowering begins early May in Southern California. Flowering extends throughout the Summer, depending on environmental conditions.
Inflorescence type and habit: Double form with conspicuous stamens. 3 to 4 whorls. Shape regularly round. Erect flower attitude. Flowers positioned just above and beyond foliar plane.
Flower longevity on plant: Approximately 10 days on the plant. Varies considerably with environmental conditions.
Quantity of flowers: 1 to 2 per stem. 5 to 9 flowering stems per plant.
Flower size:
*Diameter*.—Approximately 12 to 15 cm.
*Depth*.—Approximately 6 cm. (Flower height).
Peduncle:
*Length*.—Approximately 8 cm.
*Diameter*.—Approximately 5 mm.
*Color*.—Near RHS Yellow-Green 144C.
*Strength*.—Strong.
*Texture*.—Glabrous and ribbed.
Petals:
*Petal arrangement*.—3 to 4 whorls of about 10 to 15 petals.
*Size*.—Length.—Average 5 to 7 cm. Width: Average 4 cm.
*Shape*.—Obovate.
*Margin*.—Entire. Lightly ruffled.
*Apex*.—Emarginate.
*Base*.—Broad attenuate.
*Texture*.—Smooth, glabrous all surfaces.
*Aspect*.—Recurved up.
Color:
Petals:
*When opening*.—Opening: Upper surface: Near RHS Yellow 10D with a strong overall flush near 39A and Red 47D. Basal flare near Red 53B. Lower surface: Near RHS Yellow 10D with an overall flush near Red 39A and Red 47D. Basal flare near Red 47B. Fully opened: Upper surface: Near RHS Yellow 13D with an overall flush near Red 48C. Veins flushed Red 47D. Basal flare near Red 47B. Lower surface: Near RHS Yellow 13D with an overall flush near Red 48C. Veins flushed Red 47D. Basal flare near Red 47B. Fading: Upper surface: Near RHS Yellow 13D with a faint overall flush near Red 49C. Veins lightly flushed Red 47D. Basal flare near Red 47D. Lower surface: Near RHS Yellow 13D with a faint overall flush near Red 49C. Veins lightly flushed Red 47D. Basal flare near Red 47D.
Petaloids: Not present.
Bud:
*Shape*.—Globular.
*Length*.—Approximately 2 cm.
*Diameter*.—Approximately 2 cm.
Color.—Near RHS Yellow-Green 145B striped Red 47B.
Sepals:
*Quantity*.—2 to 4.
*Length*.—1.2 to 3.2 cm.
*Width*.—1 to 2 cm.
*Shape*.—Narrow deltate to irregular, wavy elliptic.
*Aspect*.—Flat.
*Attitude*.—Horizontal.
*Apex*.—Acute.
*Base*.—Truncate.
*Margin*.—Entire.
*Color*.—Interior Surface: RHS Yellow-Green 144A. Exterior Surface: RHS Yellow-Green 144B.
*Texture*.—Glabrous.
Fragrance: Not detected.

REPRODUCTIVE ORGANS

Androecium:
Stamens:
*Quantity*.—70 to 90, densely packed.
*Length*.—5 to 7 mm.
*Color*.—Yellow 12B.
Anthers:
*Shape*.—Linear.
*Length*.—1 mm.
*Color*.—Yellow 12B.
Gynoecium:
Pistil:
*Type*.—Compound. Petaloid, stigma only.
*Number*.—5.
*Carpel length*.—1.7 cm.
*Carpel width*.—1 cm.
*Disc color*.—Yellow-Green 144C.
*Carpel pubescence*.—Sparse.
*Openness of disc*.—Partly open.
*Stigma*.—Petaloid. 5 mm long and 4 mm in diameter. Very hard. Shape: Irregular circular. Color: Near RHS Red 53D.
*Ovary color*.—Near RHS Yellow-Green 145C flushed Red 53C.

OTHER CHARACTERISTICS

Disease and pest resistance: Observed resistance to foliar diseases of *Paeonia*. Typical foliar diseases of *Paeonia* include *Botrytis paeoniae, Graphiopsis chlorocephala* and *Phytophthora*. sp. No additional resistance nor susceptibility to the normal diseases and pests of *Paeonia* has been observed.
Temperature tolerance: Typically USDA Zones 3 to 8.
Fruit/seed production: Not observed.

What is claimed is:

1. A new and distinct cultivar of *Paeonia* plant named 'Smithopus8' as herein illustrated and described.

* * * * *